United States Patent
Hsieh

(10) Patent No.: US 12,059,399 B2
(45) Date of Patent: Aug. 13, 2024

(54) METHODS FOR ALLEVIATING KIDNEY DISEASE AND FIBROSIS OF ORGAN

(71) Applicant: Getwing Biotechnology Medical Co., Ltd, Taipei (TW)

(72) Inventor: Yi-Hsien Hsieh, Taipei (TW)

(73) Assignee: Getwing Biotechnology Medical Co., Ltd, Taipei (TW)

( * ) Notice: Subject to any disclaimer, the term of this patent is extended or adjusted under 35 U.S.C. 154(b) by 0 days.

(21) Appl. No.: 17/827,079

(22) Filed: May 27, 2022

(65) Prior Publication Data

US 2023/0012448 A1     Jan. 12, 2023

Related U.S. Application Data

(60) Provisional application No. 63/216,664, filed on Jun. 30, 2021.

(51) Int. Cl.
| | | |
|---|---|---|
| A61K 31/295 | (2006.01) | |
| A61K 9/14 | (2006.01) | |
| A61K 31/198 | (2006.01) | |
| A61K 33/26 | (2006.01) | |
| A61P 13/12 | (2006.01) | |

(52) U.S. Cl.
CPC ........... *A61K 31/295* (2013.01); *A61K 9/143* (2013.01); *A61K 31/198* (2013.01); *A61K 33/26* (2013.01); *A61P 13/12* (2018.01)

(58) Field of Classification Search
CPC .................................................. A61K 31/295
See application file for complete search history.

*Primary Examiner* — Svetlana M Ivanova
(74) *Attorney, Agent, or Firm* — HSML P.C.

(57) ABSTRACT

Disclosed herein is a method for alleviating a kidney disease or fibrosis of an organ in a subject, which includes administering to the subject a composition containing a ferrous amino acid chelate which includes ferrous ions and an amino acid.

8 Claims, 6 Drawing Sheets
(3 of 6 Drawing Sheet(s) Filed in Color)

METHODS FOR ALLEVIATING KIDNEY DISEASE AND FIBROSIS OF ORGAN

CROSS-REFERENCE TO RELATED APPLICATION

This application claims priority of U.S. Provisional Application No. 63/216,664, filed on Jun. 30, 2021.

FIELD

The disclosure relates to a method for alleviating a kidney disease and a method for alleviating fibrosis of an organ, and more particularly to a method for alleviating a kidney disease and a method for alleviating fibrosis of an organ using a ferrous amino acid chelate.

BACKGROUND

Fibrotic disorders are commonplace, take many forms and can be life-threatening. No better example of this exists than the progressive fibrosis that accompanies all chronic and/or acute renal disease. Renal fibrosis is a direct consequence of the kidney's limited capacity to regenerate after injury. Renal scarring results in a progressive loss of renal function, ultimately leading to end-stage renal failure and a requirement for dialysis or kidney transplantation. Therefore, there is a strong demand for developing agents and methods for alleviating renal fibrosis and a kidney disease associated therewith.

SUMMARY

This disclosure provides a method for alleviating a kidney disease in a subject, which includes administering to the subject a composition containing a ferrous amino acid chelate which includes ferrous ions and an amino acid.

This disclosure also provides a method for alleviating fibrosis of an organ in a subject, which includes administering to the subject a composition containing a ferrous amino acid chelate which includes ferrous ions and an amino acid.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Other features and advantages of the disclosure will become apparent in the following detailed description of the embodiments with reference to the accompanying drawings, of which.

DETAILED DESCRIPTION

Figure 1:
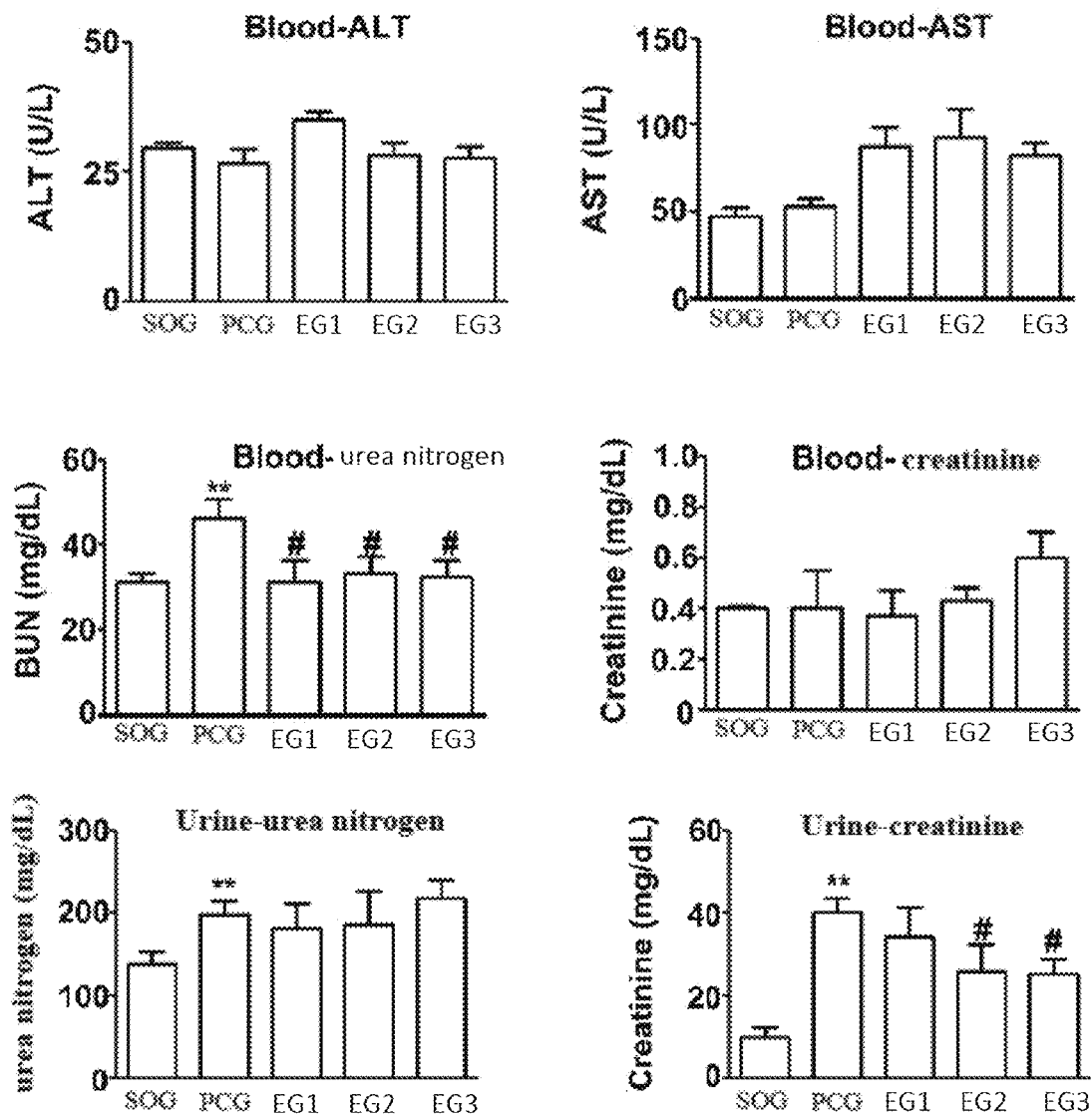
FIG. 1 shows the levels of liver enzymes, urea nitrogen and creatinine in the mice blood sample, and the levels of urea nitrogen and creatinine in the mice urine sample in each group of Example 1, infra, in which the symbol "**" represents p<0.01 compared with the normal control group (NCG), and the symbol "#" represents p<0.05 compared with the pathological control group (PCG)

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless defined otherwise, all technical and scientific terms used herein have the meaning commonly understood by a person skilled in the art to which the present disclosure belongs.

One skilled in the art will recognize many methods and materials similar or equivalent to those described herein, which could be used in the practice of the present disclosure. Indeed, the present disclosure is in no way limited to the methods and materials described.

Since the applicant has surprisingly found that a ferrous amino acid chelate is effective in alleviating kidney swelling and kidney fibrosis, the present disclosure provides a method for alleviating a kidney disease in a subject, which includes administering to the subject a composition containing a ferrous amino acid chelate which includes ferrous ions and an amino acid.

In addition, since a ferrous amino acid chelate is effective in alleviating kidney fibrosis, the applicant infers that such ferrous amino acid chelate can be used for alleviating fibrosis in an organ. Accordingly, the present disclosure provides a method for alleviating fibrosis of an organ in a subject, which includes administering to the subject the aforesaid ferrous amino acid chelate-containing composition.

In certain embodiments, the organ is selected from the group consisting of kidney, lung, liver, testicle, and combinations thereof. In an exemplary embodiment, the organ is kidney.

As used herein, the term "kidney disease" refers to a progressive loss in renal function over a period of days, months or years. Kidney disease has its general meaning in the art and is used to classify numerous conditions that affect the kidney, destruction of the renal parenchyma and the loss of functional nephrons or glomeruli. It should be further noted that kidney disease can result from different causes, but the final pathway remains renal fibrosis. Examples of etiology of kidney disease include, but are not limited to, cardiovascular diseases, hypertension, diabetes, glomerulonephritis, polycystic kidney diseases, and kidney graft rejection.

The term "fibrosis" refers to abnormal processing of fibrous tissue, or fibroid or fibrous degeneration. Fibrosis can result from various injuries or diseases, either acute or chronic, and can often result from transplant rejection relating to the transplantation of various organs. Fibrosis typically involves the abnormal production, accumulation, or deposition of extracellular matrix components, including overproduction and increased deposition of, for example, collagen and fibronectin. As used herein, the terms "kidney fibrosis", "renal fibrosis" and "fibrosis of the kidney" refer to diseases or disorders associated with the overproduction or abnormal deposition of extracellular matrix components, particularly collagen, leading to the degradation or impairment of kidney function.

The term "alleviating" as used herein means lessening, inducing stasis of, or postponing or reducing the progression, development, onset, or severity of the disease or condition or severity of one or more symptoms associated with a disease or disorder or condition described herein, or ameliorating existing uncontrolled or unwanted symptoms, preventing additional symptoms, or ameliorating or preventing the underlying metabolic causes of symptoms. Thus, the terms denote that a beneficial result has been conferred on a subject with a disease or symptom, or with the potential to develop such disease or symptom. A response is achieved when the subject experiences partial or total alleviation, or reduction of one or more signs or symptoms of disease, condition, or illness.

As used herein, the term "subject" refers to any animal of interest, such as humans, monkeys, cows, sheep, horses, pigs, goats, dogs, cats, mice and rats. In certain embodiments, the subject may be a human.

According to this disclosure, the chelating ratio of the ferrous ions to the amino acid in the ferrous amino acid chelate ranges from 1:1 to 1:4. In certain embodiments, the chelating ratio of the ferrous ions to the amino acid in the ferrous amino acid chelate ranges from 1:1.5 and 1:2.5.

The process for preparing the ferrous amino acid chelate has been disclosed in e.g. US 2017/0224727 A1 and includes the steps of mixing a ferrous compound with an amino acid under heating. In certain embodiments, the mixing step may be conducted at a temperature ranging from 60° C. to 90° C. In certain embodiments, the mixing step may be conducted for 8 hours to 48 hours.

According to the disclosure, the weight ratio of the ferrous compound and the amino acid used in the preparation process is between 1:1.2 and 1:1.5. In an embodiment of this disclosure, the weight ratio of the ferrous compound and the amino acid is 1:1.3.

In certain embodiments, the ferrous compound may be ferrous sulfate, ferrous chloride, ferrous pyrophosphate, or the combinations thereof.

In certain embodiments, the amino acid may be glycine. That is, the ferrous amino acid chelate may be ferrous glycinate chelate.

The composition according to this disclosure may be prepared in the form of a pharmaceutical composition or a food composition.

If the composition is prepared in the form of the pharmaceutical composition, the composition may further include a pharmaceutically acceptable carrier, and made into a dosage form suitable for oral administration using technology well-known to those skilled in the art. Examples of the dosage form include, but are not limited to, solution, suspension, emulsion, powder, tablet, pill, syrup, lozenge, troche, chewing gum, capsule, slurry and the like.

Examples of the pharmaceutically acceptable carrier suitable for use in this disclosure may include, but are not limited to, solvent, emulsifier, suspending agents, decomposers, binding agents, excipients, stabilizing agents, chelating agents, diluents, gelling agents, preservatives, lubricants, absorption delaying agents, liposomes, and combinations thereof.

The composition according to this disclosure may be in the form of a food additive (an exemplary example of the food composition), which can be added into an edible material to prepare a food product for human or animal consumption. Examples of the food product according to this disclosure may include, but are not limited to, fluid milk products, e.g., milk and concentrated milk; fermented milk, e.g., yogurt, sour milk and frozen yogurt; milk powder; ice cream; cream cheeses; dry cheeses; soybean milk; fermented soybean milk; vegetable-fruit juices; fruit juices; sports drinks; confectionery; jelly; candies; health foods; animal feeds; and dietary supplements.

The dosage and the frequency of administration of the composition according to this disclosure may vary depending on the following factors: the severity of the disease to be treated and the weight, age, physical condition and response of the subject to be treated. For instance, the daily dosage of the composition according to this disclosure may be 12 to 36 mg per kg of the body weight, and may be administered in a single dose or in several doses.

This disclosure will be further described by way of the following examples. However, it should be understood that the following examples are solely intended for the purpose of illustration and should not be construed as limiting the disclosure in practice.

EXAMPLE

General Experimental Materials
1. Preparation of Ferrous Amino Acid Chelate

A ferrous amino acid chelate was prepared according to the procedures described in e.g. US 2017/0224727 A1. Specifically, ferrous sulfate was mixed with glycine (above 98% purity) in a weight ratio of 1:1.3, followed by heating from 60° C. to 90° C. for 8 hours to 48 hours, so as to obtain the ferrous amino acid chelate. The chelating ratio of the ferrous irons to the amino acid (i.e. glycine) in the obtained ferrous amino acid chelate was between 1:1 and 1:4.

2. Experimental Mice

Male C57BL/6J mice (having a weight of about 25 g) purchased from the National Laboratory Animal Center (Taipei, Taiwan) were kept in an animal room under the following laboratory conditions: a temperature of about 24° C. and a 12-hour light/12-hour dark cycle. Diets and water were provided ad libitum for all of the experimental animals.

3. Source and Cultivation of Human Kidney Epithelial Cell Line (HK-2)

Human kidney proximal tubular epithelial cell line HK-2 (from normal adult human renal cortex) used in the following experiments was obtained from, the Bioresource Collection and Research Center (BCRC) of the Food industry Research and Development Institute (FIRDI) (No. 331, Shih-Pin Rd., Hsinchu City 300, Taiwan).

The HK-2 cells were incubated in 10-cm Petri dishes, each of which contained Dulbecco's modified Eagle's medium/Ham's Nutrient Mixture F-12 (DMEM/F12) (Manufacturer: Thermo Fisher Scientific, WA, USA; Catalogue no.: 12500062) supplemented with HyClone™ 1% (v/v) penicillin-steptomycin (Manufacturer: Cytiva; Catalogue no.: SC30010). Subsequently, cultivation was conducted in an incubator with culture conditions set at 37° C. and 5% $CO_2$. Medium change was performed every 2 days. When reaching 85% of confluence, the cultured cells were subjected to sub-culturing.

General Experimental Procedures
1. Unilateral Ureter Obstruction (UUO) Surgery

The UUO surgery was performed in accordance with the Guidelines for Care and Use of Laboratory Animals. Specifically, during the UUO surgery, the respective mouse was anesthetized through intraperitoneal injection of pentobarbital (Manufacturer: Merck KGaA, Darmstadt, Germany; Catalogue no.: P3761) at a dose of about 60 mg per kg of body weight. The skin tissue and the subcutaneous muscle layer at the left side of the abdominal midline were incised, so that the left kidney was exposed and the left ureter was identified and dissociated. The left ureter was dissected out with scissors and ligated with silk surgical sutures (size: 4-0) at an upstream location approximately 1 cm from the renal hilum and at a downstream location approximately 1 cm from the renal hilum. After confirmation that no bleeding and no urine leakage occurred, the incised subcutaneous muscle layer and skin tissue were stitched.

2. Statistical Analysis

All the experiments described below were performed in triplicates. The experimental data of all the test groups are expressed as mean±standard deviation (SD), and were analyzed using unpaired two-tailed Student's t-test using GraphPad Prism 4 software (Developer: GraphPad Software, Inc., San Diego, CA) and SPSS 12.0 (Developer: International Business Machine Corporation), so as to assess the differences between the groups. Statistical significance is indicated by $p<0.05$.

Example 1. Evaluation of the Effect of Ferrous Amino Acid Chelate on Alleviating Renal Fibrosis A. Biochemical Analysis of Blood and Urine Samples Methods:

The male C57BL/6J mice described in section 2 of the "General Experimental Materials" were randomly divided into 5 groups, namely, a sham-operated group (SOG), a pathological control groups (PCG), and three experimental groups (i.e., experimental group 1 (EG1), experimental group 2 (EG2), and experimental group 3 (EG3)) (n=3 per group). After being raised in the animal room for one week, the mice in the PCG and the EG1 to EG3 were subjected to the UUO surgery as described in section 1 of the "General Experimental Procedures". The mice in the SOG were subjected to a similar surgical procedure, except that the ureter of the mice in the SOG was not obstructed, i.e., the left ureter was not dissected out and ligated. After surgery, during the entire experimental process which lasted 7 days, all the mice were placed in iron cages.

The mice of the EG1 to EG3 were respectively administered, via oral gavage, with the ferrous amino acid chelate described in section 1 of the "General Experimental Materials" at a dose of 5 mg/kg, 125 mg/kg and 250 mg/kg of body weight once daily (in the morning) for 7 days. At the end of Day 7, a blood sample and a urine sample, each in a volume of 0.2 mL, were obtained from each mouse in the EG1 to EG3. The mice of the SOG and the mice of the PCG received no treatment (i.e., 0 mg/kg of ferrous amino acid chelate), and at the end of Day 7, a blood sample and a urine sample, each in a volume of 0.2 mL, were obtained from each mouse.

The blood sample of the respective mouse was subjected to measurements of alanine transaminase (ALT), aspartate transaminase (AST), blood urea nitrogen (BUN) and creatinine levels for evaluation of kidney health. The urine sample of the respective mouse was subjected to quantification of urea nitrogen and creatinine levels for evaluation of kidney health. For each of the aforesaid parameters, the differences between each group were analyzed according to the procedures as described in the section 2 of the "General Experimental Procedures".

Results:

FIG. 1 shows the levels of ALT, AST, urea nitrogen and creatinine in the blood sample (upper panel), and the levels of urea nitrogen and creatinine in the urine sample (lower panel) of the mice of each group 7 days after the UUO surgery. As shown in the upper panel of FIG. 1, the blood urea nitrogen level in the PCG was significantly higher than that in the SOG, indicating that the UUO surgery adversely affected the renal function of the mice. In addition, the blood urea nitrogen level determined in each of EG1 to EG3 was significantly reduced compared to that in the PCG, and was even similar to that in the SOG. Moreover, no significant difference was observed on the blood urea nitrogen level among the EG1 to EG3. Furthermore, for each of the ALT, AST, and creatinine levels in the blood samples, no significant difference were observed between the SOG, PCG, and EG1 to EG3.

As shown in the lower panel of FIG. 1, the urine creatinine level and urine urea nitrogen level in the PCG were significantly higher than those in the SOG, indicating that the UUO surgery adversely affected the renal function of the mice. In addition, the urine creatinine levels determined in EG2 and EG3 were significantly reduced compared to that in the PCG, whereas no significant difference was observed on the urine urea nitrogen level among the PCG, EG1, EG2 and EG3.

These results demonstrate that the ferrous amino acid chelate of the present disclosure is effective in alleviating renal fibrosis caused by UUO surgery and improving renal function.

B. Observation of Renal Morphology

Methods:

After collecting the blood and urine samples, the mice in each group described in section A of this example were sacrificed. The left and right kidneys of the respective mouse were collected. The left obstructed kidneys of the PCG, and EG1 to EG3 were visually compared to those of the SOG for observation of renal morphology.

Figure 2:
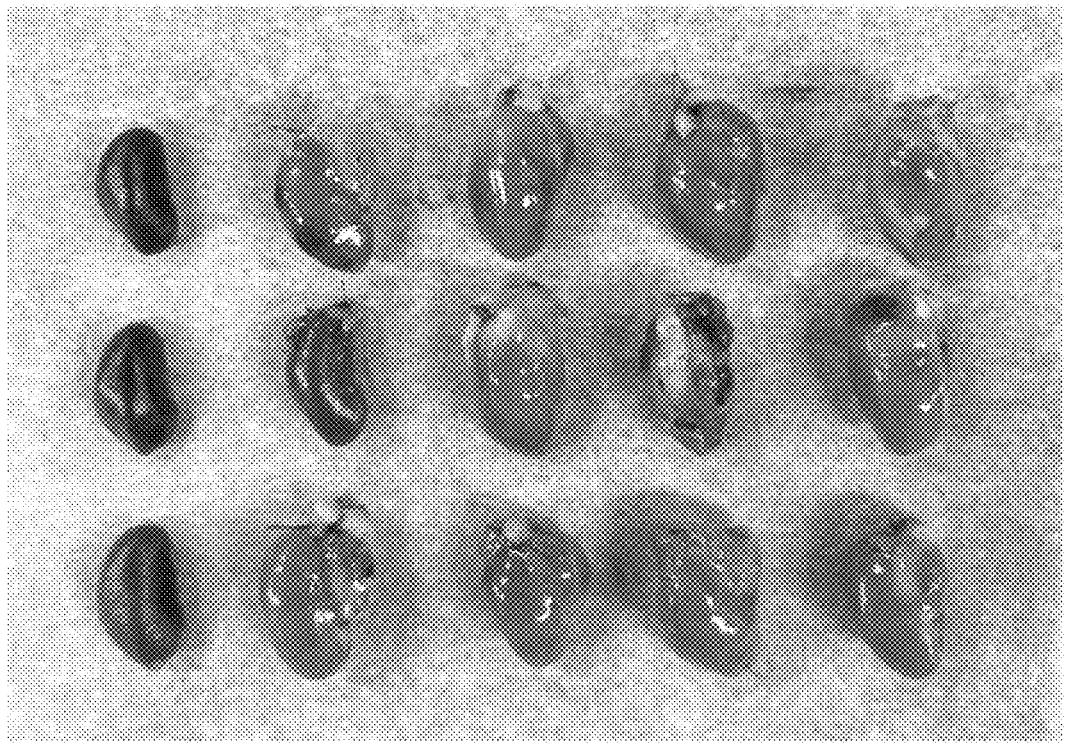
FIG. 2 shows the kidney morphology of the mice in each group of Example 1, infra.

Results:

FIG. 2 shows the kidney morphology of the mice in each group 7 days after the UUO surgery. As shown in FIG. 2, the left obstructed kidneys of the mice in the PCG exhibited a higher degree of gross morphological changes (e.g., hypertrophy, hydronephrosis, tubular dilation, and interstitial expansion) compared to those of the mice in the SOG 7 days after the UUO surgery, indicating that renal fibrosis was induced by the UUO surgery.

C. Histological Analysis for Renal Tissues

Methods:

The renal tissues were extracted from the left obstructed kidney of a selected mouse in each group. Fixation was conducted using 10% formalin, and dehydration was conducted using a series of graded alcohols (lower to higher concentrations) and xylene, followed by embedding in paraffin. A tissue section of 4 mm was obtained and placed on a slide, followed by heating in an oven at 37° C. overnight for melting the paraffin. Xylene was used to remove the melted paraffin, and rehydration was conducted with graded alcohols (higher to lower concentrations). Endogenous peroxidase was removed using 1% $H_2O_2$, followed by washing with a phosphate-buffered saline (PBS) buffer, so as to increase the permeability. After incubating the tissue section with fetal bovine serum (FBS) to prevent binding of some non-specific antigens, water was removed by suction.

For staining of α-smooth muscle actin (SMA), a primary antibody against α-smooth muscle actin (SMA)(α-SMA) (Manufacturer: Abcam PLC; Catalogue no.: ab5694) with a dilution ratio of 1:400 was added to the tissue section at room temperature, and the reaction was allowed to proceed for 2 hours at room temperature. Thereafter, washing was conducted twice with PBS to remove unbound primary antibodies. A Polymer-HRP secondary antibody (Manufacturer: Golden Bridge International, Inc., USA) was added. One hour later after the reaction, washing was conducted twice with PBS. An avidin-biotin complex (ABC) solution was added, and the reaction was allowed to proceed for 45 minutes at room temperature, followed by washing with PBS twice, α-smooth muscle actin (SMA) was identified based on brown color distribution in the stained tissue section.

Nuclear staining was performed by immersing the tissue section in a substrate buffer for 10 minutes. After the reaction was quenched, Surgipath®) Hematoxylin Gill II solution (Manufacturer: Leica Biosystems Inc.; Catalogue no.: 3801522) and Surgipath® Eosin Y solution (Manufacturer: Leica Biosystems Inc.; Catalogue no.: 3801602) were added, and then ddH$_2$O was applied to wash the excessive staining solution. Dehydration was performed using an alcohol, followed by adding dropwise a mounting medium onto the slide and covering the side with a cover slip. The nucleus were identified based on blue color distribution in the stained tissue section.

Staining of interstitial collagen fibers and muscle fibers were performed on the tissue section using the Trichrome Stain Kit (Modified Masson's) (Manufacturer: ScyTek Laboratories, Inc.; Catalogue no.: TRM-2-IFU) according to the manufacturer's instructions. The collagen fibers and muscle fibers were respectively identified based on blue color and red color distribution in the stained tissue section.

For staining of vimentin, which serves as a marker for cells under pathological conditions, particularly cells undergoing fibrosis, the tissue section were subjected to immunohistochemical analysis with support provided by personnel from Rapid Science Co. Ltd., Taiwan. To be specific, a primary antibody against vimentin (Manufacturer: Cell Signaling Technology, Inc.; Catalogue no.: #5741) with a dilution ratio of 1:50 was added at room temperature, and the reaction was allowed to proceed for 2 hours at room temperature. Thereafter, washing was conducted twice with PBS to remove unbound primary antibodies. A polymer-HRP goat anti-rabbit IgG H&L secondary antibody (Manufacturer: Abcam PLC, Cambridge, UK; Catalogue no.: ab214880) was added. One hour later after the reaction, washing was conducted twice with PBS. The vimentin were identified based on brown color distribution in the stained tissue section.

The respective stained tissue section was subjected to imaging and photography using a fluorescence microscope (Manufacturer: Carl Zeiss Microscopy, LLC, USA; Model no.: Axio Imager. A2 (490022-0009-000)) at a magnification of 100×.

Figure 3:
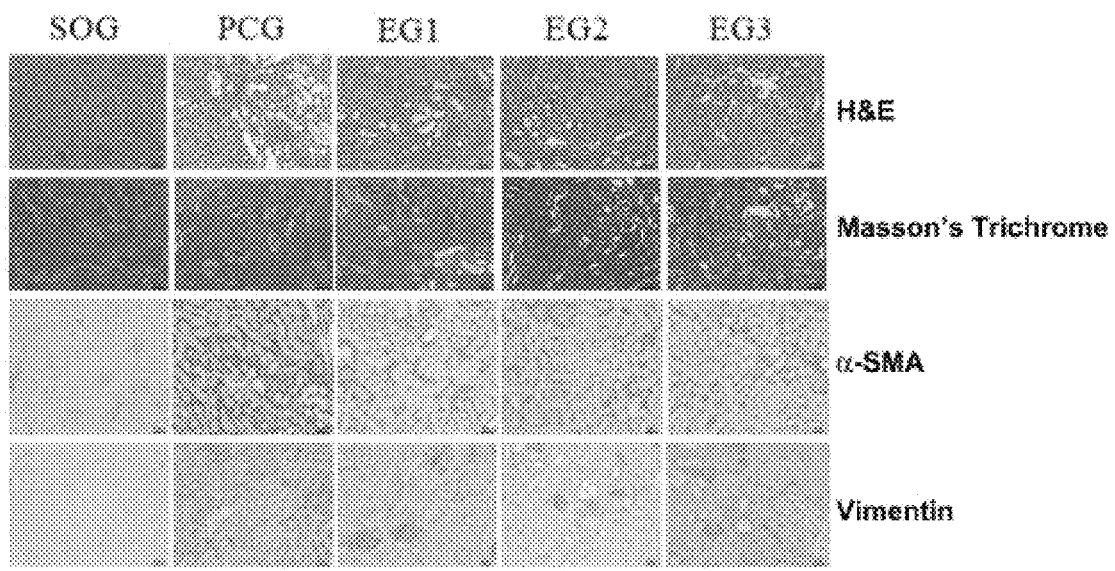
FIG. 3 shows the histological analysis of kidney tissue sections of the selected mice in each group of Example 1, infra.

Results:

FIG. 3 shows the histological analysis of kidney tissue sections of the selected mice in each group 7 days after the UUO surgery. As shown in FIG. 3, the tissues of the left obstructed kidney of the selected mouse of the PCG exhibited a higher degree of tubular dilation as indicated by hematoxylin and eosin (H & E) staining, an increased interstitial deposition of collagen fibers and muscle fibers as indicated by Masson's Trichrome staining, an increased amount of actin fibers as indicated by α-SMA staining, and an increase in the number of cells undergoing fibrosis as indicated by vimentin staining compared to those of the selected mouse of the SOG 7 days after the UUO surgery, confirming that tubulointerstitial fibrosis was induced by the UUO surgery. In addition, the tubular dilation, interstitial deposition of collagen fibers and muscle fibers, amount of actin fibers, and the number of cells undergoing fibrosis in each of EG1 to EG3 were significantly reduced compared with those in the PCG, and the degree of reductions of tubular dilation, and interstitial deposition of collagen fibers and muscle fibers were greater in EG2 and EG3 compared with those in EG1. These results indicate that the ferrous amino acid chelate of the present disclosure is capable of alleviating renal fibrosis.

D. Protein Expression Analysis for Renal Tissues Methods:

The renal tissues were extracted from the left obstructed kidney of a selected mouse in each group, and then lysed with NETN lysis buffer (20 mM Tris, 150 mM NaCl, 1 mM EDTA, and 0.5% NP-40) on ice. The resultant cell lysates were centrifuged, and the supernatants were collected to serve as total protein samples.

Protein samples in equal amounts (i.e., 20 μg) as determined by Bradford assay were resolved in 8% or 10% sodium dodecyl sulfate-polyacrylamide (SDS-PAGE) gels, and then subjected to immunoblot analysis. To be specific, the separated proteins were transferred to Immobilon®-P polyvinylidene difluoride (PVDF) membranes (Manufacturer: Merck Millipore, NJ, USA). The blotted PVDF membranes thus obtained were blocked with Tris-buffered saline (TBS) and 0.1% (vol/vol) polysorbate 20 (also known as Tween 20) containing 5% non-fat dry milk for 1 hour at room temperature, followed by washing with TBST 3 times, each time for minutes, and then probing with the indicated primary antibodies overnight. The probed membranes were washed with a TBST buffer (a mixture of TBS and polysorbate 20) 3 times, each time for 5 minutes, and were then incubated with secondary antibodies, such as a horseradish peroxidase (HRP)-conjugated anti-mouse antibody or an HRP-conjugated anti-rabbit antibody for 60 minutes at room temperature. HRP was detected using ECL detection reagents (Merck Millipore, Darmstadt, Germany), and band intensity was determined by ImageQuant™ LAS-4000 luminescence image analyzer (GE Healthcare).

The primary and secondary antibodies used for detecting the respective protein are shown in Table 1 below. Anti-glyceraldehyde 3-phosphate dehydrogenase (GAPDH) was used as a loading control.

TABLE 1

| Proteins | Primary antibody; dilution factor | Secondary antibody |
|---|---|---|
| Vimentin | Rabbit polyclonal anti-vimentin antibody (Manufacturer: BioVision, Inc., Milpitas, CA, USA; Cat. no.: #3634-100); 1:1000 | AffiniPure goat anti-rabbit IgG (H + L), HRP-linked antibody (Manufacturer: Jackson ImmunoResearch Laboratories, West Grove, PA, USA; Cat. no.: 111-035-003) |
| α-smooth muscle actin (α-SMA) | Mouse monoclonal anti-SMA antibody (Manufacturer: Santa Cruz Biotechnology, Inc., CA, USA; Cat. no.: sc-32251); 1:500 | AffiniPure goat anti-mouse IgG (H + L), HRP-linked antibody (Manufacturer: Jackson ImmunoResearch Laboratories, West Grove, USA; Cat. no.: 115-035-003) |

TABLE 1-continued

| Proteins | Primary antibody; dilution factor | Secondary antibody |
|---|---|---|
| Collagen I | Rabbit monoclonal anti-collagen I antibody (Manufacturer: Cell Signaling Technology, Inc., Danvars, MA, USA; Cat. no.: #72026); 1:1000 | AffiniPure goat anti-rabbit IgG (H + L), HRP-linked antibody (Manufacturer: Jackson ImmunoResearch Laboratories, West Grove, USA; Cat. no.: 111-035-003) |
| Anti-glyceraldehyde 3-phosphate dehydrogenase (GAPDH) | Mouse monoclonal anti-GAPDH antibody (Manufacturer: Santa Cruz Biotechnology, Inc., CA, USA; Cat. no.: sc-32233); 1:5000 | AffiniPure goat anti-mouse IgG (H + L), HRP-linked antibody (Manufacturer: Jackson ImmunoResearch Laboratories, West Grove, USA; Cat. no.: 115-035-003) |

Figure 4:
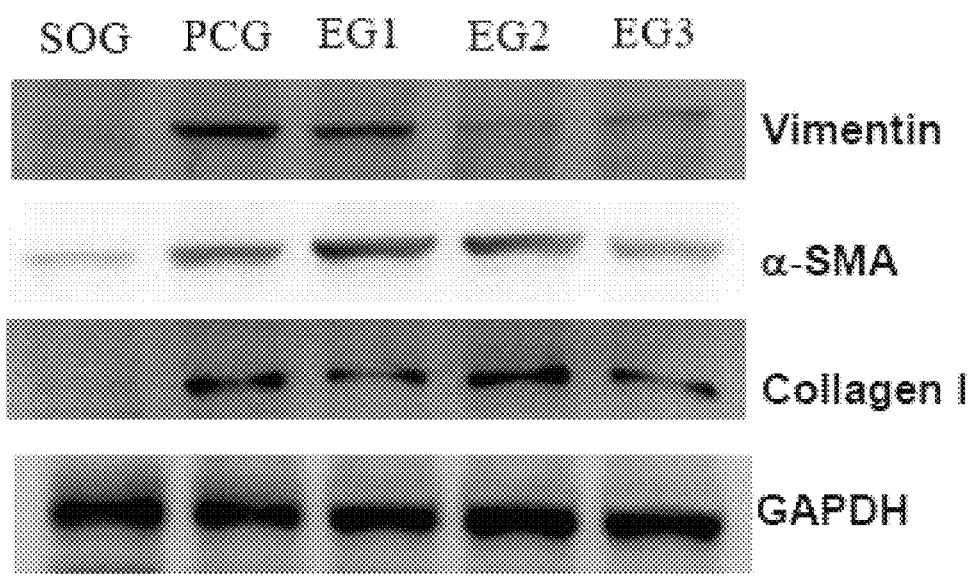
FIG. 4 shows the protein expression levels of α-smooth muscle actin, collagen fibers, and vimentin in kidney tissues in each group of Example 1, infra, in which GAPDH served as a loading control.

Results:

FIG. 4 illustrates Western blot results of fibrous proteins (i.e., α-SMA, collagen I fibers, and vimentin) in kidney tissues in each group 7 days after the UUO surgery. As shown in FIG. 4, in comparison with SOG, the expressions of vimentin, α-SMA and collagen I fibers were increased in the PCG, indicating that renal fibrosis occurred after UUO surgery. In addition, the expression level of vimentin was gradually reduced from EG1 to EG3 compared to that in the PCG, and the EG2 and EG3 showed a significant reduction in expression level compared to that in the PCG. Moreover, the expressions of α-SMA and collagen I were significantly reduced in EG3 compared to that in PCG, while no significant difference was observed among the EG1, EG2 and PCG. These results suggest that the ferrous amino acid chelate of the present disclosure, when administered in a dosage of 250 mg/kg, is capable of reducing the expression of fibrous proteins in the kidney.

Collectively, these results indicate that the ferrous amino acid chelate of the present disclosure is effective in alleviating kidney fibrosis.

Example 2. Cytotoxicity Analysis of the Ferrous Amino Acid Chelate

Methods:

First, the HK-2 cells described in section 3 of the General Experimental Materials were seeded at a concentration of $2 \times 10^4$ cells per well into wells of 6-well culture plates each containing DMEM/F-12 supplemented with 1% (v/v) penicillin-steptomycin, and then were divided into 7 groups, namely, a control group (CG), and six experimental groups (i.e., experimental groups 1 to 6 (EG1 to EG6)), followed by cultivation in an incubator with culture conditions set at 37° C. and 5% $CO_2$ for 24 hours. Next, each of the cell cultures of the EG1 to EG6 were treated with the ferrous amino acid chelate having a corresponding one of concentrations of 50, 100, 250, 500, 750 and 1000 μg/mL, while the cell culture of the CG received no treatment. After 24 hours of incubation, the culture medium of each group was removed, and the cells were washed with phosphate-buffered saline (PBS) twice, and then incubated with a MTT reagent at a concentration of 0.5 mg/mL for 4 hours. Thereafter, the MTT reagent was removed, and the cells were incubated with 1 mL of isopropanol at room temperature for 5 minutes. Subsequently, the medium in each group was collected and subjected to light absorbance measurement at a wavelength of 570 nm ($OD_{570}$) using a spectrophotometer.

The cell viability rate (%) of each group was calculated using the following Equation (I):

$$A = (B/C) \times 100 \qquad (I)$$

where A=cell viability rate (%)
B=$OD_{570}$ value of respective group
C=$OD_{570}$ value of control group The differences between the groups were statistically analyzed according to the procedures described in section 2 of the General Experimental Procedures.

Figure 5:
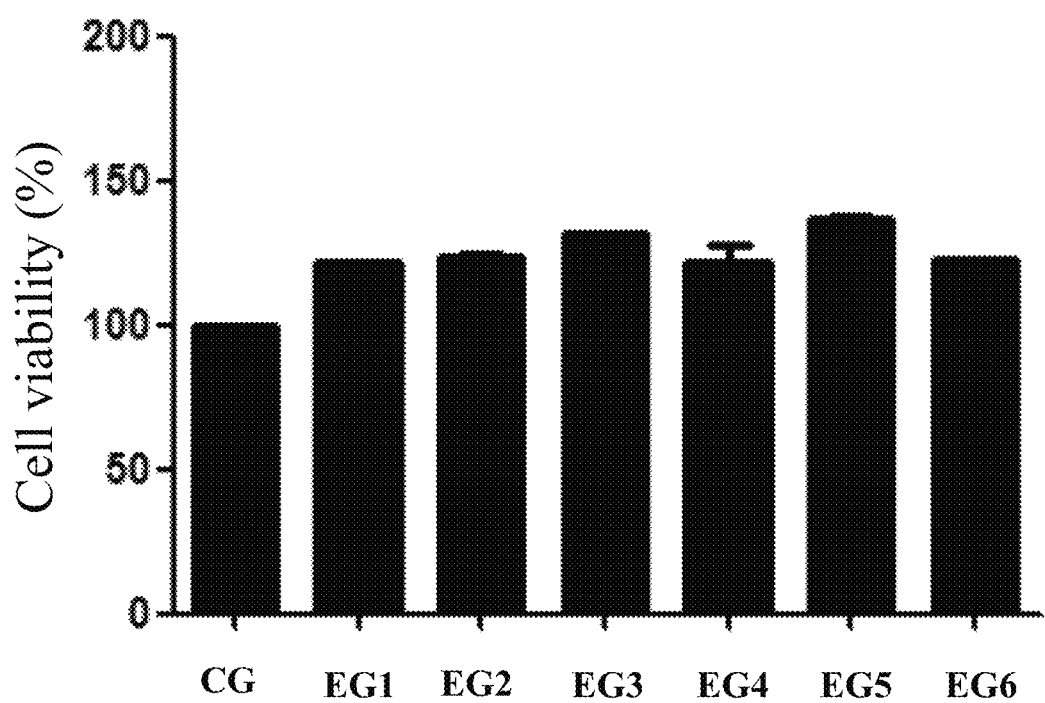
FIG. 5 shows the viability percentage of HK-2 cells in each group of Example 2, infra.

Results:

FIG. 5 shows cell viability rate of HK-2 cells in each group after treatment with the ferrous amino acid chelate. As shown in FIG. 5, the viability of the HK-2 cells in each of EG1 to EG6 was not significantly affected as compared to that in the CG, indicating that cytotoxicity is not induced after treating the renal tubular epithelial cells with the ferrous amino acid chelate of the present disclosure.

Example 3. Evaluation of the Effect of Ferrous Amino Acid Chelate on Alleviating Renal Fibrosis Induced by TGF-β1

Methods:

First, the HK-2 cells described in section 3 of the General Experimental Materials were seeded at a concentration of $4 \times 10^4$ cells per well into wells of 6-well culture plates each containing DMEM supplemented with 1% (v/v) penicillin-steptomycin, and then were divided into 4 groups, namely, a control group, a comparative group 1, a comparative group 2, and an experimental group, followed by cultivation until reaching 90% of confluence. Next, the cell culture of each group was scraped along the diameter of the corresponding well by using a 200 μL pipette tip to create a cell-free wound area of approximately 50 μm. Then, the culture medium was removed, and a fresh culture medium (i.e., serum-free DMEM) and 2 μg/mL of mitomycin c (serving as a cell proliferation inhibitor) was added to the cells in each group. Thereafter, the cells in the comparative group 1 were treated with 50 ng/mL of transforming growth factor beta-1 (TGF-β1) (Source: a recombinant human TGF-β1 protein purchased from R&D systems, Inc.; Catalogue no.: 240-B), the cells in the comparative group 2 were treated with 100 μg/mL of ferrous amino acid chelate, and the cells in the experimental group were treated with 50 ng/mL of TGF-β1 and 100 μg/mL of ferrous amino acid chelate. The cells in the control group received no treatment. Cell migration was assessed at the 0 hour and $24^{th}$ hour using an inverted optical microscope.

Figure 6:
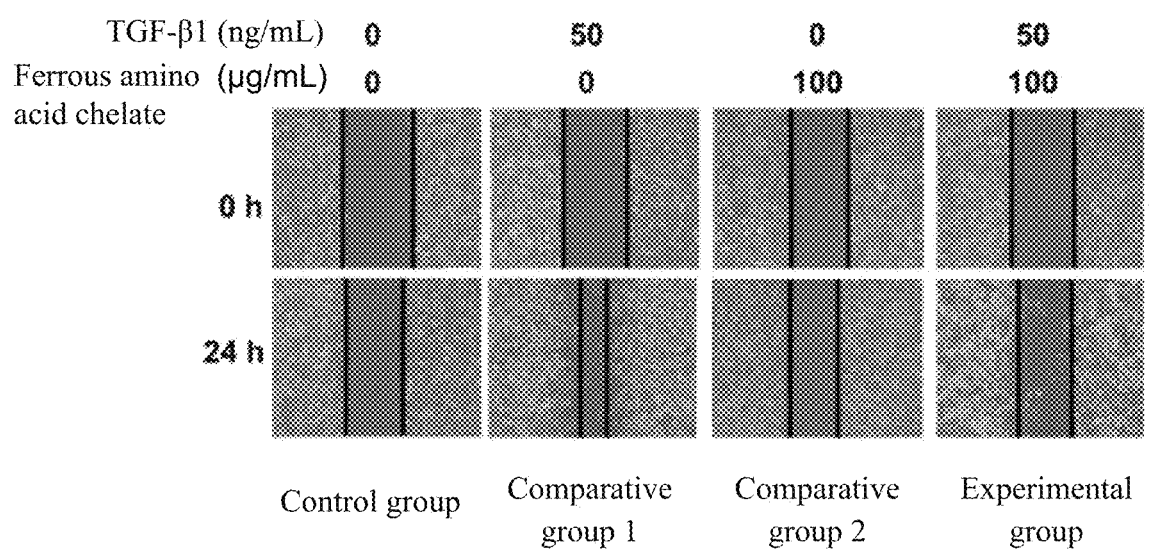
FIG. 6 shows the migration of HK-2 cells in each group of Example 3, infra.

Results:

FIG. 6 are optical microscopy images showing migration of HK-2 cells in each group. As shown in FIG. 6, after 24 hours, the HK-2 cells in the comparative group 1 acquired an increased migratory behaviour (i.e., move away from their epithelial cell community) into the cell-free wound area as compared to those in the control group, confirming that the HK-2 cells were induced to undergo epithelial-mesenchymal transition (EMT) process by TGF-β1. In contrast, the HK-2 cells in the experimental group showed a decreased capability to migrate into the cell-free wound area as compared to those in the comparative group 1, indicating that the ferrous amino acid chelate of the present disclosure is capable of inhibiting the EMT process induced by TGF-β1. Since EMT is recapitulated under pathological conditions, such as fibrosis, this result suggest that the ferrous amino acid chelate of the present disclosure is capable of alleviating renal fibrosis.

Taken together, these results demonstrate the therapeutic effect of the ferrous amino acid chelate of the present disclosure on renal fibrosis. Hence, the ferrous amino acid chelate of the present disclosure is expected to be useful in alleviating a kidney disease (e.g., an acute kidney disease) and fibrosis of an organ such as kidney.

All patents and literature references cited in the present specification as well as the references described therein, are hereby incorporated by reference in their entirety. In case of conflict, the present description, including definitions, will prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A method for alleviating fibrosis of an organ in a subject in need thereof, comprising administering to the subject a composition comprising a ferrous amino acid chelate.

2. The method of claim 1, wherein the ferrous amino acid chelate is ferrous glycinate chelate.

3. The method of claim 1, wherein the chelating ratio of ferrous ions to amino acid in the ferrous amino acid chelate ranges from 1:1 to 1:4.

4. The method of claim 1, wherein the composition is orally administered.

5. The method of claim 1, wherein the organ is selected from the group consisting of kidney, lung, liver, testicle, and combinations thereof.

6. The method of claim 5, wherein the organ is kidney.

7. The method of claim 5, wherein the fibrosis is associated with a kidney disease.

8. The method of claim 7, wherein the kidney disease is an acute kidney disease.

* * * * *